United States Patent [19]
Krause et al.

[11] Patent Number: 6,053,922
[45] Date of Patent: Apr. 25, 2000

[54] FLEXIBLE SHAFT

[76] Inventors: William R. Krause, 820 Gilliams Mountain Rd., Charlottesville, Va. 22903; Garland U. Edwards, 4247 Ketcham Dr., Chesterfield, Va. 23832

[21] Appl. No.: 08/680,628

[22] Filed: Jul. 17, 1996

Related U.S. Application Data

[60] Provisional application No. 60/006,064, Oct. 23, 1995, and provisional application No. 60/001,475, Jul. 18, 1995.

[51] Int. Cl.⁷ ................................................ A61B 17/32
[52] U.S. Cl. ............................ 606/80; 606/180; 464/78
[58] Field of Search ................................ 606/80, 85, 84, 606/79, 81, 96, 130; 464/78, 54, 57, 58, 59, 97; 408/210, 199

[56] References Cited

U.S. PATENT DOCUMENTS

| | | |
|---|---|---|
| 2,515,366 | 7/1950 | Zublin . |
| 4,646,738 | 3/1987 | Trott . |
| 4,706,659 | 11/1987 | Matthews et al. . |
| 4,751,922 | 6/1988 | DiPietroopolo . |
| 5,108,411 | 4/1992 | McKenzle . |
| 5,122,134 | 6/1992 | Borzone et al. . |
| 5,387,218 | 2/1995 | Meswania ................................. 606/80 |
| 5,488,761 | 2/1996 | Leone . |
| 5,527,316 | 6/1996 | Stone et al. ............................... 606/80 |

OTHER PUBLICATIONS

"New Twists for Flexible Shafts", Paul Dvorak, Machine Design, Sep. 7, 1989 p.145–146.
"Flexible Shafts Make Obstacles Disappear", Jul. 1993, Figure 1 Brian Parlato, S.S. White Technologies Inc., Power Transmission Design.
Suhner Catalog pp. 6,15 & 16 "Flexible Shafts Spiral Bevel Gears", Undated.
S.S. White Technologies Inc. Catalog p. 4–5 "Ready–Flex", Undated.

*Primary Examiner*—Michael Buiz
*Assistant Examiner*—David O. Reip
*Attorney, Agent, or Firm*—Sheldon H. Parker

[57] ABSTRACT

An improved flexible shaft used in the reaming of the medullary space in bones is described. The shaft is comprised of a solid element with a longitudinal bore the entire length and an appropriately formed slot which extends spirally around the shaft either continuously or segmentally. Attached to the shaft's opposite ends respectively, are a cutting head and a means of connecting the shaft to a driving mechanism.

21 Claims, 7 Drawing Sheets

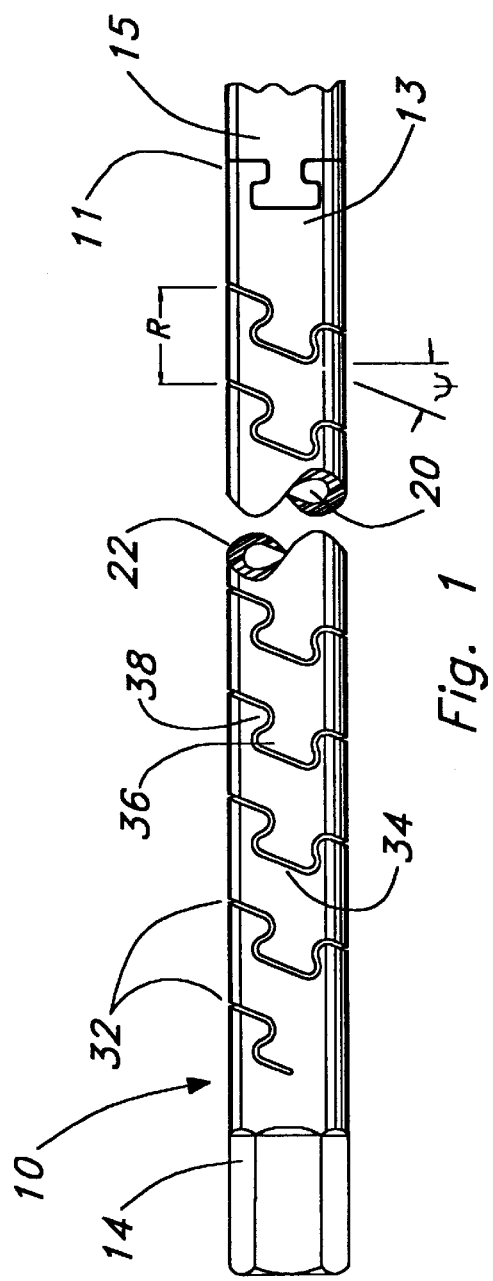
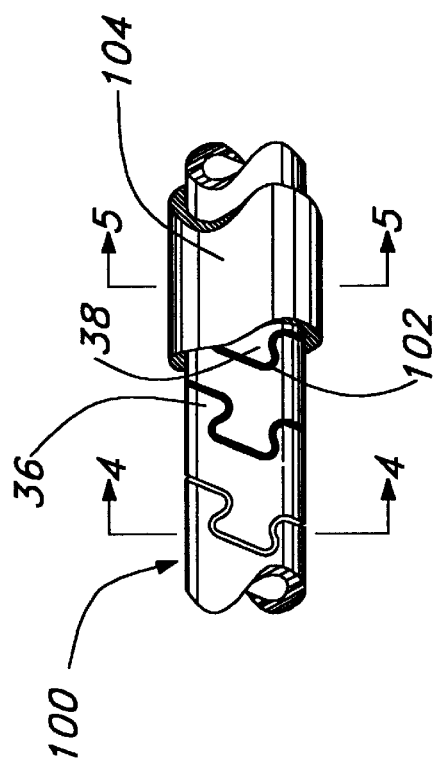

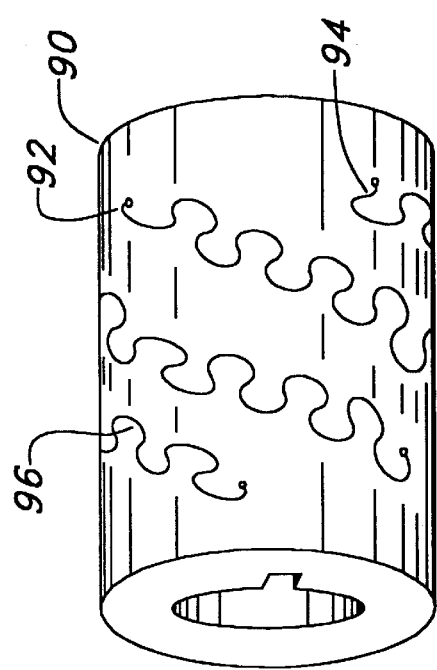
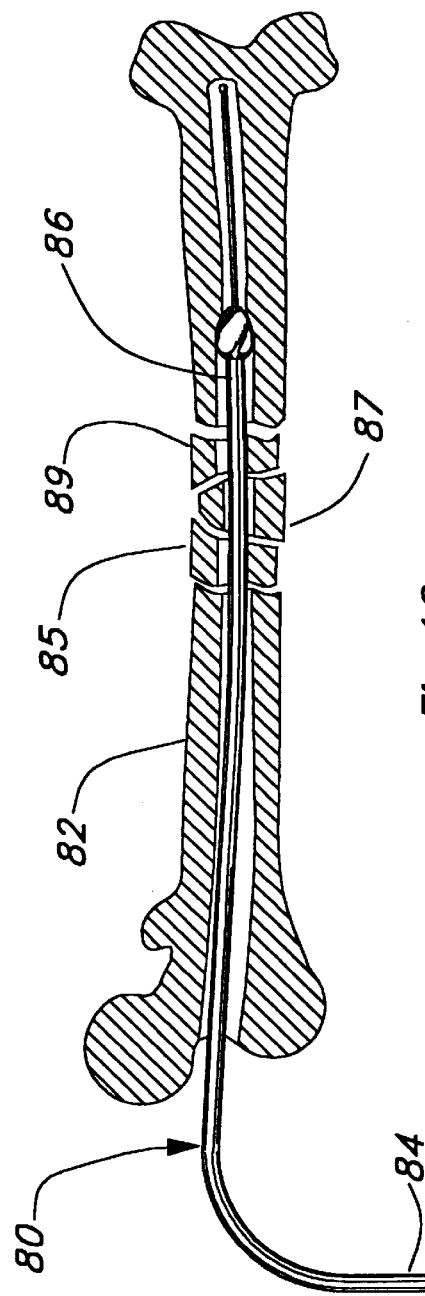

FLEXIBLE SHAFT

CROSS REFERENCE TO RELATED APPLICATIONS

This application is a continuation in part of copending provisional patent application, Ser. No. 60/006,064 filed Oct. 23, 1995 and copending provisional application Ser. No., 60/001,475 filed Jul. 18, 1995, the subject matters of which are incorporated herein, by reference, as though recited in full.

BACKGROUND OF THE INVENTION

1. Field of the Invention

This invention relates to flexible shafts and couplings; specifically to an improved flexible shaft for the transmission of rotary motion and power around, over or under obstacles. The invention specifically includes an improved flexible shaft for the purpose of reaming the medullary canal of bones.

2. Brief Description of the Prior Art

Flexible shafts and couplings are used to transmit rotary power between a power source and a driven part when a straight, unobstructed path is unavailable. A flexible shaft generally consists of rotating shaft with end fittings for attachment to mating parts, typically a power source and the driven part, as depicted in FIG. 3 of U.S. Pat. No. 4,646,738, Suhner catalog at page 6, and the S. S. White Technologies Inc. catalog, page 4, (1994). A protective outer casing may be used to protect the shaft when necessary. Flexible shafts are used in numerous applications anywhere the transmission of rotary power is necessary and a straight unobstructed path is unavailable, as depicted in the S. S. White Technologies Inc. catalog, page 5 and Suhner at page 6. Flexible shafts have been used in children's toys to aerospace applications. Examples of the usage of flexible shafts have been presented in the articles "New Twists for Flexible Shafts" (Machine Design, Sep. 7, 1989), in particular pages as illustrated on pages 145 and 146, and "Flexible Shafts Make Obstacles Disappear" (Power Transmission Design, July, 1993), in particular FIG. 1. One example cited was a safety valve, located 30 ft. off the ground and not readily accessible, that had to be operated on a daily basis to remain operable, but was not exercised as regularly as required due to the difficulty in reaching it. With the installation of a flexible shaft from the valve to floor level, personnel were able to operate the valve regularly and verify its proper function. Flexible shafts are used on aircraft to raise and lower wing flaps, slats, and leading and trailing edges. Stainless steel flexible shafts allow surgeons greater maneuverability with bone cutting and shaping tools. Flexible shafts are also used extensively to compensate for less than perfect alignment between a driver and a driven component. The limitation for the use of flexible shafts are limitless and is only limited by the torque capabilities of the shaft.

The principle application of a flexible shaft is to transmit rotary motion and power in a curvilinear manner. Flexible shafts are used when there is little or no accurate alignment between the power source and the driven part; when the path between the power source and the driven part is blocked or is in an environment or position which would not allow the power source; for the connection or driving of components which have relative motions; and to dampen and absorb vibration both from the drive unit and the driven tool.

Heretofore, flexible shafts and couplings available for power transmission consisted of single or multiple wires wound over a central drive core or a hollow core, as illustrated in U.S. Pat. No. 5,108,411, FIG. 2, and as depicted in the Suhner publication, pages 15 and 16. The number of wires per layer and the number of layers will vary according to the application and requirements for either unidirectional or bidirectional torque power transmission. Typically wire wound flexible shafts are designed and manufactured to be operated in only one direction of rotation; either clockwise or counter clockwise, when viewed from the driving end. They are designed to maximize the torque carrying capabilities for the direction of rotation for which they were designed. The performance of a unidirectional shaft operated in the reverse direction is significantly less than the intended performance levels.

A specific application of flexible shafts is with flexible medullary canal reamers. Medullary canal reamers are used to enlarge the medullary canal of bones in preparation for the insertion of prosthetic components, such as a total hip prosthesis, the insertion of fracture reduction and fixation devices, such as intramedullary nails, performing an intramedullary osteotomy, the insertion of a plug to preclude bone cement from migrating while in its viscous state, stimulating bone growth, and for other purposes. Since the medullary canal is irregular in internal diameter and configuration from end to end it is preferred by the surgeon to enlarge the medullary canal to a more uniform diameter or to a diameter that will allow passage or insertion of the intended device. Because the shafts of long bones are bent or curved along their longitudinal axes, flexible shafts that can bend to follow this naturally curved path while transmitting the necessary torque required to cut the bone are necessary.

Should a straight, rigid, or inflexible shaft be used in the reaming process to enlarge the canal, there is considerable likelihood that the reamer will not follow the natural curvature of the bone, will not remove the desired amount of bone and will not produce a uniform internal diameter. In addition, should a straight, rigid reamer be used, there is a high degree of likelihood that the reamer will jam, cause excessive bone removal or penetrate the outer integrity of the bone. For this reason, medullary canals are almost always prepared with reamers having a flexible shaft. Flexible medullary reamers are of such design that utilizes a central bore intended to receive a long, small diameter guide rod or wire which is initially inserted into the medullary canal. The guide wire or rod establishes a track for the advancing reamer. However, the use of a flexible reamer does not preclude the problem of jamming or reamer stoppage when the cutting head of the reamer gets caught by the bony structure and does not turn. A jammed cutting head may be extremely difficult, if not impossible to dislodge or remove without further violation of the involved bone or breakage of the reaming device. The preferred method to dislodge the reamer would be to reverse the reamer. However, the design of the most widely used devices prevent the reversal of the reamer without destruction of the flexible shaft.

Heretofore, the flexible medullary shaft reamers available to the orthopedic surgeon are of three types: (i) a shaft with a plurality of parallel flexible elements or rods joined together at opposite ends by means of a welded of soldered connection, (ii) a shaft comprised of a spiral or helically wound metal wire(s) or strip(s), and (iii) a shaft comprised of a series of inter-engaged links, assembled over a guide rod.

The first distinct type of flexible medullary reamer (i) embodies a plurality of parallel, flexible elements joined together at opposite ends. A disadvantage of this shaft occurs during usage as the reamer rotates causing the elements to become twisted and thereby to become more rigid and reduce the shaft's flexibility. Another disadvantage of said reamer is the shaft's tendency, as it rotates but is not yet fully within the confines of the medullary canal, to tear tissue from underlying structures as the individual elements are torsionally loaded and unloaded, thereby enlarging and contracting the spaces between the individual wires to trap uninvolved tissue and tearing them free. Another disadvantage of said flexible reamer occurs during insertion of the reamer over the guide rod. The central bore is intended to receive the small diameter guide rod. Except at its respective ends, this reamer lacks a well defined and bordered central bore. Therefore it is difficult to prevent the guide rod from exiting the reamer in the area of the free standing elements during the insertion of the guide wire. A further disadvantage of this flexible shaft is the inefficient transfer of energy from the power source to the cutting head which is caused by the twisting and wrapping together of the individual elements as the reamer is rotated. Another disadvantage of this type of reamer is that it is extremely noisy during operation due to the multiple elements hitting one another during the rotation.

The second distinct type of flexible medullary reamer (ii) consists of spiral or helically wound metal wires or strips. This is the most widely used flexible shaft for intramedullary reaming. The major disadvantage of this reamer design is that it can only be operated in the forward mode of operation. If the cutter becomes jammed and the surgeon reverses the reamer to dislodge the cutter or to facilitate removal, the shaft unwinds, thus rendering the reamer permanently deformed, unusable, and unrepairable. A further disadvantage of this medullary reamer is that the torsional load to which it is subjected when in use results in poor power transfer and varying degrees of distortion of said shaft. If the power source providing the rotational energy to the reamer is great enough, said coils may tighten sufficiently to adversely affect the structural integrity of the shaft and cause the shaft to permanently deform into a helical shape. A further disadvantage of this type of reamer is the inability to clean the shaft and the cavities within the helically wound strips of surgical debris after the operation for the prevention of cross contamination between patients. If infectious blood or body fluids infiltrates the mechanism of the device, it is extremely difficult to remove and clean.

The third distinct type of flexible shaft (iii) consists of a series of inter-engaged links assembled over a guide wire. A distinct disadvantage of this design is during usage and interchanging the cutting head. The current usage of this design dictates that the links are held together by a longitudinal guide wire over which the linkages are assembled. In order to change the cutting head, a flexible tube must be inserted through the central bore of the linkages, and the assembled links must be taken off the centralizing guide wire. In the process linkages frequently become unassembled and require the surgeon to reassemble the linkages.

U.S. Pat. No. 5,488,761 to Leone, shows prior art spiral wound flexible shafts using a single shaft and a pair of reverse wound shafts. The patent also discloses materials of construction for the shaft and a mechanism for cleaning the slot, after it is cutting. Alternate cutting technologies are also disclosed.

The prior art is depicted in Matthews, U.S. Pat. No. 4,706,659 which show two modifications of prior art devices, in FIGS. 1 and 2. The device of Matthews is loosely related to the present invention in that it is a mechanism for providing a flexible connecting shaft for an intramedullary reamer. While the proposed solution to the problem is different from that of the present invention, the patent discloses the importance of a flexible connection and discloses reamer structures. The disclosure of Matthews U.S. Pat. No. 4,706,659 is incorporated by reference herein, as though recited in full.

U.S. Pat. No. 4,751,922 (DiPietropolo) also shows the importance of flexible medullary reamers and explains some of the prior art problems. The patent also discloses the use of a hollow core 2, for receiving a guide pin.

U.S. Pat. No. 5,122,134 (Borzone et al) is incorporated by reference as though recited in full and is noted to disclose in FIG. 5, the use of a guide pin 55.

FIG. 1 of Zublin, U.S. Pat. No. 2,515,365 illustrates a flexible drill pipe for use in the drilling of well bores. Additional Zublin patents include U.S. Pat. Nos. 2,515,366, 2,382,933, 2,336,338 and 2,344,277. The drill pipe is a helically slotted flexible drill pipe having a slot varying from 3/32 of an inch (0.0938") to 5/32 of an inch (0.1563") in width and having a pitch of the spiral of about nine inches for a four and one-half inch diameter drill pipe (helix angle of 32.48 deg). Zublin indicates that the described flexible resilient drill pipe has the capacity to bend into a curve of an eighteen foot diameter utilizing a repeating "dovetail" pattern of over six cycles per revolution, for use with four and one half inch diameter drill pipe. In the instant invention, it has been found that shafts of one inch or less require the use of a helix angle of approximately one half that described by Zublin and that the number of repeating cycles of the interlocking pattern is less than the shown six cycles per revolution. For the smallest of flexible shafts describe, the use of about two pattern repetitions (cycles) per spiral revolution is more appropriate.

Accordingly it is an object of this invention to provide a flexible shaft which will flex, bend or curve to follow the natural intramedullary canal of the bone while transmitting reaming torque.

It is a further object of this invention to provide a flexible shaft which may be operated both in the forward and reverse directions therefore with equal effectiveness.

It is a further object of this invention to provide a flexible shaft which will have considerable rotational or torsional stiffness so that it will not store and then irregularly release rotational energy.

It is a further object of the invention to provide a flexible shaft which will be of a single one unit which does not have to be assembled from multiple units.

It is another object of this invention to provide a flexible shaft which will flex, bend or curve while transmitting torque.

It is a further object of this invention to provide a flexible shaft which may be operated both in the clockwise and counter clockwise directions therefore with equal effectiveness.

It is a further object of this invention to provide a flexible shaft which will have considerable rotational or torsional stiffness so that it will not store and then irregularly release rotational energy.

It is a further object of the invention to provide a flexible shaft which will be of a single unit which does not have to be assembled from multiple units.

It is a further object of the invention to provide a flexible coupling which will flex, bend or curve while transmitting torque.

These and other objects, features, advantages and aspects of the present invention will be better understood with reference to the following detailed description of the preferred embodiments when read in conjunction with the appended drawing figures.

SUMMARY OF THE INVENTION

The present invention overcomes the deficiencies and problems evident in the prior art as described herein above by combining the following features into an integral, longitudinally flexible and torsionally inflexible shaft.

A flexible shaft is provided for the transmission of rotary power from a drive power unit to a driven unit. The driven unit can be a drill bit, a surgical reamer, a pump, or any similar device. The flexible shaft is an elongated tubular member of substantial wall thickness. The diameter of the shaft is preferably in the range from about 0.15 inch to about 4.00 inch. The ratio of the diameter of the inside diameter of the shaft to the outside diameter of the shaft is advantageously in the range from about 1:1.2 to about 1:3, and preferably is in the range from about 1:1.3 to about 1:4. The thinner the wall of the shaft, the more critical is the configuration of the slot.

Advantageously, the slot is cut at an angle normal to the shaft using a computer controlled cutting technique such as laser cutting, water jet cutting, milling or other means. Additionally, this slot may be cut at an angle to the normal so as to provide an undercut slot, preferably the angle is in the range from about 30 to about 45 degrss from the normal.

A slot of substantial length and width extends in a generally helical path, either continuously or intermittently, around and along the tubular member. The slot follows a serpentine path along the helical path generally around and along the tubular member, corresponding generally to the form of a signal wave on a carrier wave, that is, an amplitude modulated carrier wave.

A plurality of slots, can be employed thereby increasing the flexibility of the shaft, relative to a shaft having a single slot of identical pattern. The serpentine path forms a plurality of teeth and complimentary recesses on opposite sides of the slot. The slot has sufficient width to form an unbound joint permitting limited movement in any direction between the teeth and the recesses, thereby providing limited flexibility in all directions upon application of tensile, compressive, and/or torsion forces to said shaft.

The flexible shaft can have different degrees of flexibility along the length of said shaft. The varied flexibility can be achieved by having the pitch of the helical slot vary along the length of the shaft. The varied flexibility corresponds to the variation in the pitch of the helical slot. The helical path can have a helix angle in the range of about 10 degrees to about 45 degrees, and the helix angle can be varied along the length of the shaft to produce correspondingly varied flexibility. Alternatively, the width of the helical slot can vary along the length of the shaft to provide the varied flexibility. Advantageously, the width of the slot is preferably in the range from about 0.005 inch to 0.075 inch. Preferably the width of the slot is in the range from about 0.01 to about 0.05 inch. The rigidity of the flexible shaft can be achieved through the design of the slot pattern, thereby enabling the use of thinner walls than would otherwise be require to produce equivalent rigidity. In a preferred embodiment, the ratio of the amplitude of the serpentine path to the pitch of the slot is in the range from greater than 0.1 to about 0.5.

The slot can be filled with a resilient material, partially or entirely along the path of the slot. The resilient material can be an elastomer compound which can be of sufficient thickness to fill the slot and to encapsulate the entire shaft thus forming an elastomer enclosed member. The elastomer can be a resilient material such as a urethane or a silicone compound.

In a preferred embodiment the driven unit is a medullary canal reamer, for use in reaming the medullary canal of bones. In this application, the foregoing slot patterns and shaft dimensions, are particularly critical.

Preferably, the flexible shaft, is formed by laser cutting an elongated tubular member of substantial wall thickness, to form the slot around and along the tubular member. The serpentine path can form of a generally sinusoidal wave superimposed on a helical wave.

Preferably, the sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

BRIEF DESCRIPTION OF THE DRAWINGS

These and other objects, features, advantages and aspects of the present invention will be better understood with reference to the following detailed description of the preferred embodiments when read in conjunction with the appended drawing figures.

FIG. 1 is a schematic representation of a flexible shaft of the present invention;

FIG. 2 is a schematic representation of the spiral slit of FIG. 1, showing coated and uncoated regions;

FIG. 11 is a perspective view of a flexible coupling using the spiral slit of the present inventio and showing a plurality of spirals slots; and FIG. 12 is a schematic and cut away view of the shaft employed in reamering a medullary canal of a femur.

DEFINITIONS AND TERMS

Figure 5:
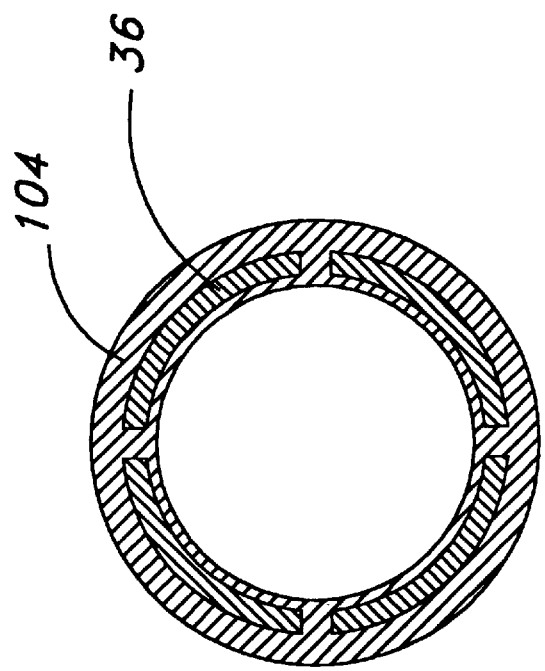
FIG. 5 is a schematic representation of a flexible cable with a resilient filler in a portion of the slot.

The term slot as used herein, is defined in the American Heritage Dictionary, 3rd Edition, Copyright 1994, as follows:
The terms slit and slot are used interchangeably, consistent with their definitions, as follows:
  slot n.
    1. A narrow opening; a groove or slit: a slot for coins in a vending machine; a mail slot.

2. A gap between a main and an auxiliary airfoil to provide space for airflow and facilitate the smooth passage of air over the wing.

The term pitch as used herein, is defined in the American Heritage Dictionary, 3rd Edition, Copyright 1994, as follows:

pitch—n.
1. The distance traveled by a machine screw in one revolution.
2. The distance between two corresponding points on adjacent screw threads or gear teeth.

The term helix angle, angle ψ in FIG. 1, as used herein, shall define the angle formed between the plane perpendicular to the longitudinal axis of the shaft and the helical path of the spiral along the shaft. The term helix angle can also be defined mathematically as the arc tangent of the pitch of the helix divided by the circumference of the shaft.

The terms used herein are intended to have their customary meanings as set forth in the American Heritage Dictionary, 3rd Edition, Copyright 1994.

Cycle-1. An interval of time during which a characteristic, often regularly repeated event or sequence of events occurs: Sunspots increase and decrease in intensity in an 11-year cycle.

2.a. A single complete execution of a periodically repeated phenomenon: A year constitutes a cycle of the seasons.

2b. A periodically repeated sequence of events: cycle includes two halves of the sine-wave like undulation of the slot path.

Spiral 1a.

A curve on a plane that winds around a fixed center point at a continuously increasing or decreasing distance from the point.

1b. A three-dimensional curve that turns around an axis at a constant or continuously varying distance while moving parallel to the axis; a helix.

1c. Something having the form of such a curve: a spiral of black smoke.

2. Printing. A spiral binding.

3. Course or flight path of an object rotating on its longitudinal axis.

4. A continuously accelerating increase or decrease: the wage-price spiral.

Spiral (adj.)
1. Of or resembling a spiral.
2. Circling around a center at a continuously increasing or decreasing distance.
3. Coiling around an axis in a constantly changing series of planes; helical.

The term amplitude, as used herein the maximum absolute value of the periodically varying quantity of the slot 30.

The spiral is more explicitly a helix-like, in that it is a three-dimensional curve that lies on a cylinder, so that its angle to a plane perpendicular to the axis is constant. However, along the length of the shaft, the helix angle may vary so as to impart changes in flexibility to the overall shaft. Using an electronics analogy, the helix can be viewed as a carrier wave with the slot following the path of the modulation of the carrier wave. The teeth or interlocking regions of the cycle, form a ratchet-like structure, in that one set of teeth engage the other set of sloping teeth, permitting motion in one direction only.

The term frequency, the number of times a specified phenomenon occurs within a specified interval, as stated in the American Heritage Dictionary, 3rd Edition, Copyright 1994:

Frequency.
1a. Number of repetitions of a complete sequence of values of a periodic function per unit variation of an independent variable.
1b. Number of complete cycles of a periodic process occurring per unit time.
1c. Number of repetitions per unit time of a complete waveform, as of an electric current.

The number of times the cycles form a repetitive pattern in one unit of length is the frequency of the slot pattern.

The number of cycles "C" of the slot undulations superimposed upon the helical path which are present in one revolution around the shaft, is referred to as the cycles per revolution.

As used herein the term serpentine refers to the undulations of the cut in any geometric configuration whether it is dovetailed, mating or winding fashion.

DETAILED DESCRIPTION OF THE PREFERRED EMBODIMENTS

The shaft of the device of the present invention, indicated generally as 10 as illustrated in FIG. 1 includes an end 14 provided for attachment to a drive means such as an electric or gas driven motor. At the other end 13, of the device 10 includes a connection member 11 providing for attachment to a driven part 15 such as a tool, gearbox, or connecting shaft. The device 10 includes a longitudinal bore 20 spanning from the end 13 to the end 14 thus providing a channel for passage of wires and other instrumentation, as well known in the art and discussed above. The device 10 includes a slot 32 cut through the wall 22 of the shaft 10, so as to form a serpentine path which extends generally along the path of a spiral around the shaft 10, as shown in Zublin, U.S. Pat. No. 2,515,365, as dotted line 20, FIG. 1.

When employing the flexible shaft 10 for the transmission of power from the driven end 14 to the driven part 15, the serpentine slot 32 along the spiral path permits the device 10 to bend along the longitudinal axis of the device 10. The dovetail configuration of the serpentine slot 32 is composed of teeth 36 and 38. Teeth 36 and 38 will effectively interlock the sections of the dovetail 34 above and below the teeth 36 and 38 and will thereby transmit torque.

Where the device is to be used as a flexible shaft for power transmission, the shaft typically has a diameter less than an inch but may be larger depending upon the specific application. The slot characteristics shown in U.S. Pat. No. 2,515,365 cannot be applied to this application. A one inch or less shaft must have a lower helix angle of the helical path, a higher spiral frequency and fewer cycles of slot undulations about the helical path to provide the required combination of structural strength and flexibility.

Figure 4:
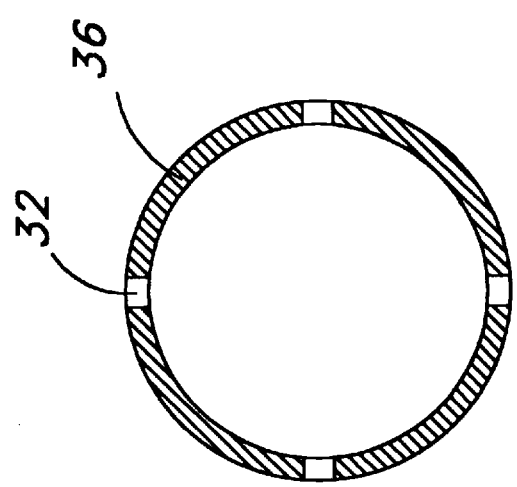
FIGS. 3 and 4 are schematic illustrations showing the angle of the slot.
Figure 3:
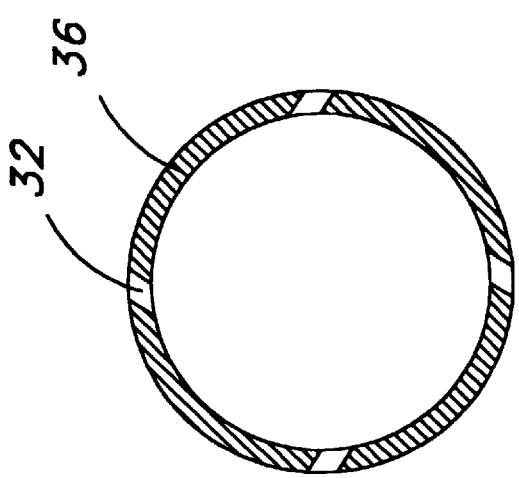

Advantageously, the slot is cut perpendicular to a plane tangent to the outer surface of the shaft as shown in FIG. 3. Alternatively, the slot can be cut at some angle to the longitudinal axis of the shaft and/or the plane tangent to the outer surface, as shown in FIG. 4. The angle can be in the range from zero (perpendicular) to about 75 degrees thereby forming an undercut. Preferably the angle if not perpendicular, is in the range from about 30 to 45 degrees from the perpendicular. The undercut can be formed by cutting offset from the radius, or offsetting from a plane tangential to the surface of the shaft at the slot.

Additionally, in a preferred embodiment, the body of the shaft has a high level of flexibility to facilitate movement around, over or under an obstacle. The preferred embodiment can be constructed in such a manner to provided varying degrees or segments of customized flexibility. Variations in flexibility can most readily be achieved by varying the length of the region which is cut with the spiral slots as well as varying the angle of the slot relative to the long axis of the shaft. Thus, where high flexibility is required a longer length of spiral slot can be used and a greater region length cut. Where less flexibility is required, a short slot length can be used. Customization enhances the ability to drive the shaft in a straight line where required, to negotiate around, over or under obstacles and/or to be driven by a rotary power source whose axis is substantially out of line with the axis of the driven part.

Whereas FIG. 1 of Zublin, 2,515,365 illustrates over six cycles per revolution, for use with four and one half inch diameter drill pipe, in the instant invention, it has been found that shafts of one inch or less requires the use of one to four cycles per revolution depending upon the shaft diameter. Thus, the change in shaft diameter does not result in a proportional change in size of the slot pattern. It has been found that the lower number of helical cycles per revolution produces greater resistance to fracture under torque while providing a less flexible shaft. Most preferably, flexible shafts have a helix angle of less than twenty degrees, in order to produce the required balance between flexibility and structural strength. The range is preferably from about 15 to 20 degrees resulting in a pitch equal to the diameter of the shaft. While the use of a small helix angle, resulting in a higher number of revolutions per unit shaft length, is not preferred unless a very flexible shaft is desired, fewer revolutions per unit length can be used where less flexibility is required. For example, in the varying flexibility flexible shaft, the number of revolutions can be reduced in the relatively rigid regions, as compared to the higher flexibility regions. As shown in FIG. 2, the flexible shaft indicated generally as 100 has the advantage of providing an ability to be routed around, over or under an obstacle, connect to a moving obstacle, provide connection with an unaligned component or to a part in a harsh environment requiring power. The use of a highly flexible shaft 86 permits for ease of guiding the required power to be transmitted to the required part.

The advantage of such a variable flexible shaft, is for a control shaft that must be snaked around different sized obstacles. In sections requiring a smaller radius of curvature, the disclosed shaft can be manufactured for highest flexibility. When variable flexibility is required, the shaft can be cut in restricted areas, or regions, with parts of the shaft remaining uncut. This produces a straight, non-flexible region. The larger the radius of curvature, the less flexible the shaft. The pitch, pattern and length of each region cut can vary within parts of the shaft to provide varying flexibility.

FIG. 1 shows the helix angle, ψ, of the spiral. The smaller the angle, the larger the number of revolutions "R" of the helical path, per inch and the greater the flexibility of the shaft.

Figure 6A:
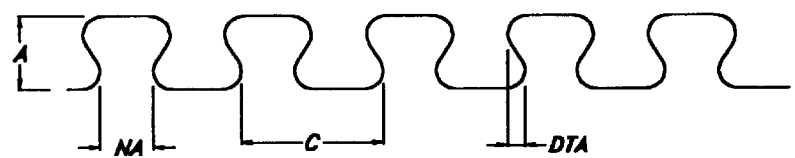
FIGS. 6A–6K show schematic representations of additional spiral slit patterns.
Figure 6B:
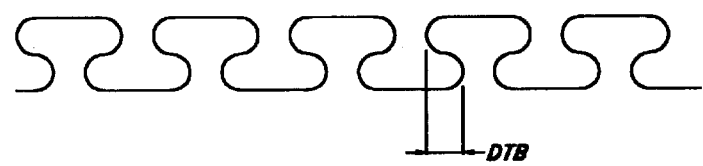
Figure 6C:
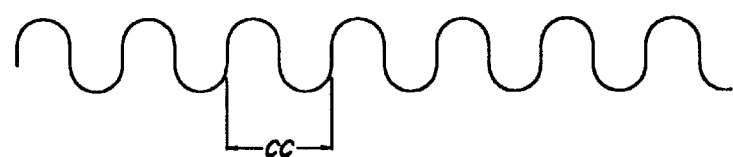
Figure 6D:
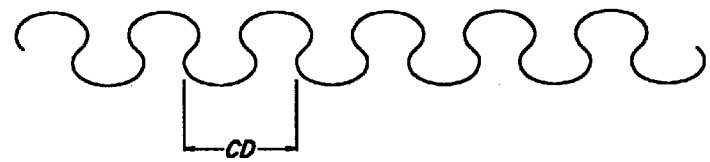
Figure 6E:
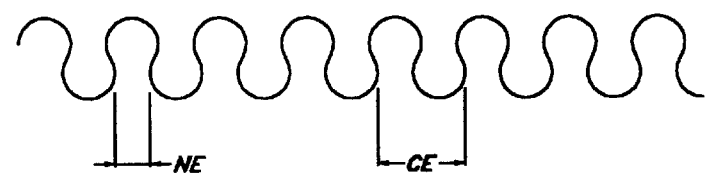
Figure 6F:
Figure 6G:
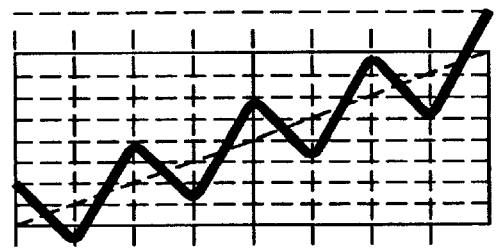
Figure 6H:
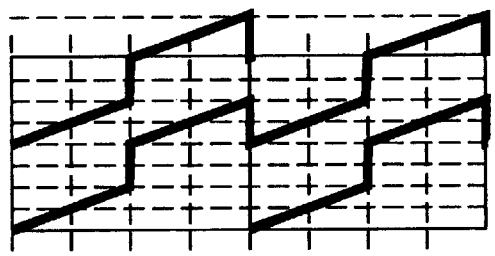
Figure 6I:
Figure 6J:
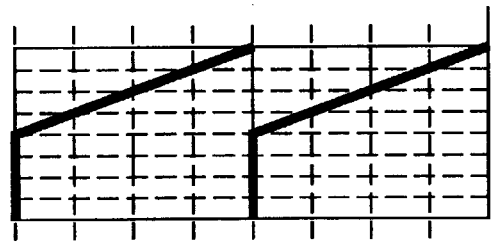
Figure 6K:
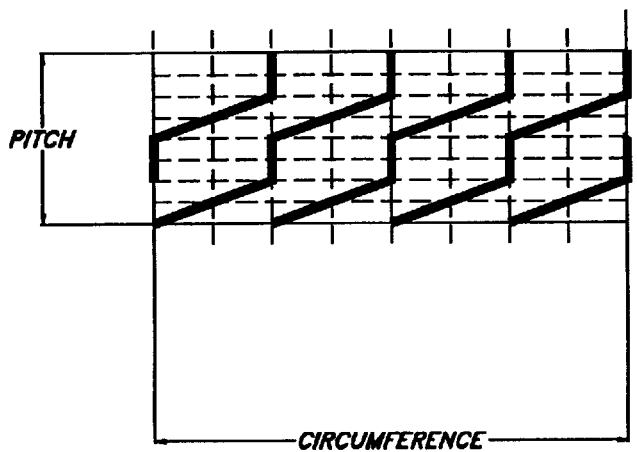

A variety of slot patterns are illustrated in FIG. 6A–K. The patterns are representative of patterns which can be used and are not intended to be all inclusive. As illustrated in FIG. 6A, the pattern has a cycle length C, which includes a neck region NA. The wider the neck region the greater the strength of the connector, that is, the greater the torsional forces which the flexible shaft can transmit. The ability of the device to interlock is dependent in part upon the amount of overlap or dovetailing, indicated as DTA for FIG. 6A and DTB for FIG. 6B. The pattern of 6C, does not provide dovetailing, and requires a helix angle which is relatively small. FIG. 6D illustrates a segmented, elliptical dovetail configuration with CD indicating the cycle of repetition. In FIG. 6E the ellipse has been rounded out to form a circular dovetail cut with CE indicating the repetitive cycle and the cut pattern of FIG. 6F is a dovetailed frustum. The pattern of FIG. 6G is a sine wave pattern forming the helical path. FIG. 6H is an interrupted spiral in which the slot follows the helical path, deviates from the original angle for a given distance, and then resumes the original or another helix angle. FIG. 6I is the same pattern as FIG. 6H, however in FIG. 6H there are two lead cuts while in FIG. 6I there is a single lead cut. FIGS. 6J and 6K show two dimensions of the same pattern having multiple leads.

Figure 7A:
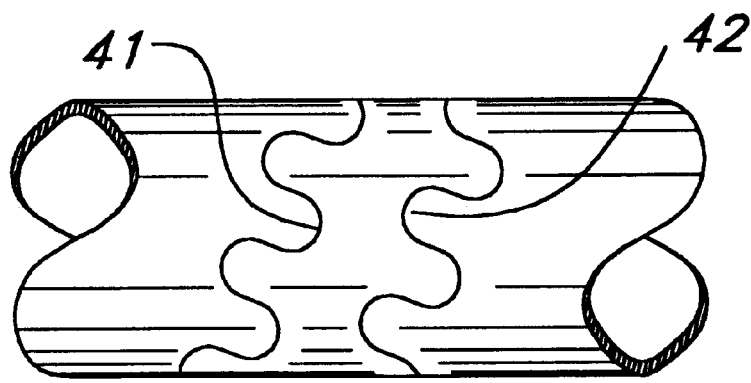
FIGS. 7A–7C are schematic side views showing spiral slits having various numbers of cycles per revolution, that is, differents pitches.
Figure 7B:
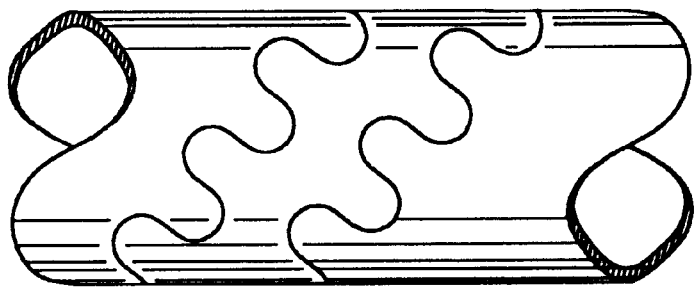
Figure 7C:
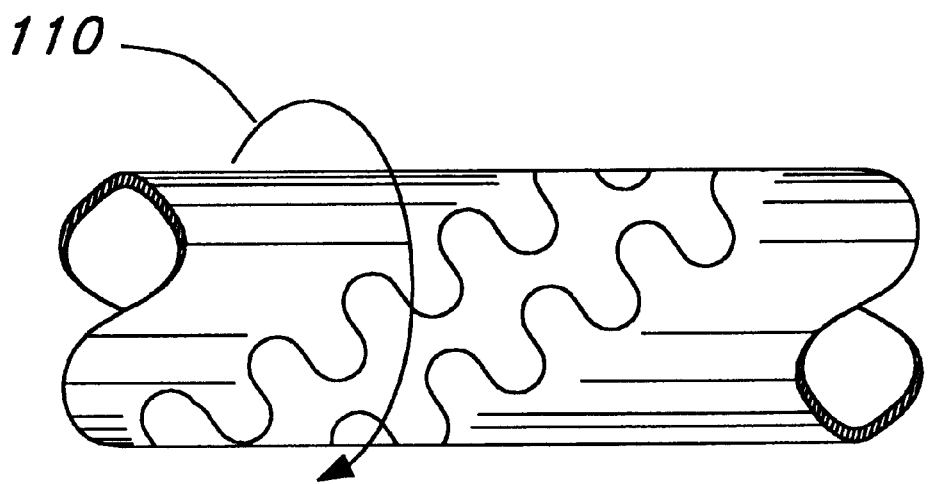

As shown in FIG. 7C, rotation in the direction of arrow 110 can open the spiral. The steeper angles of FIGS. 7B and 7C provide progressively greater resistance to opening, even without the dovetailing effect being present. It should be noted that in certain patterns, it is preferred to provide an odd number of cycles per revolution, as shown in FIGS. 7A, 7B and 7C. In this manner the peak point of the cycle 41, is out of phase with the peak point 42 of the next revolution. In these embodiments when the two points are in phase, the amount of material between the two points is so small as to provide an adequate structural strength. Obviously, the use of a steep helix angle, that is, a very low number of cycles per revolution can be used to provide adequate space between the peak points 41 and 42.

The flexible shaft can be produced by any convenient means. Computer controlled milling or cutting, wire electrical discharge machining, water jet machining, spark erosion machining, and most preferably laser cutting is most conveniently used to produce the desired pattern. The advantages of computer controlled laser cutting are the infinite variety of slot patterns which can be produced, the ability to change the helix angle at any point along the shaft, the variations with respect to slot width, and the overall precision afforded, as compared to conventional cutting mechanisms. The combination of laser cutting with the slot patterns of this inventions, can produce customized shafts having not only a predetermined flexibility, but also predetermined variations in flexibility, while providing substantially uniform characteristics with counterclockwise and clockwise rotation.

Figure 8:
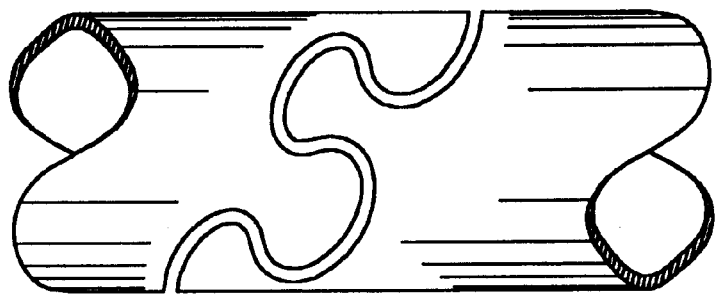
FIG. 8 is a fragmentary side view of the embodiment of FIG. 7, showing the gap formed by the slit.
Figure 9:
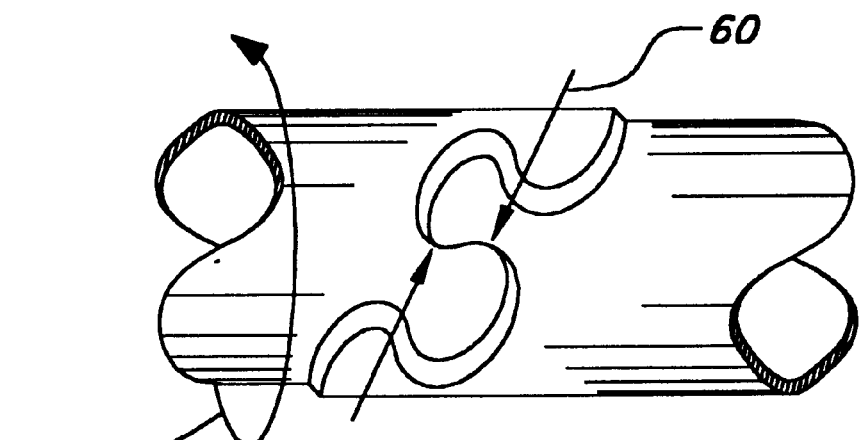
FIG. 9 is a fragmentary side view of the embodiment of FIG. 8, showing a section of the device of the present invention after being torqued in the clockwise direction.
Figure 10:
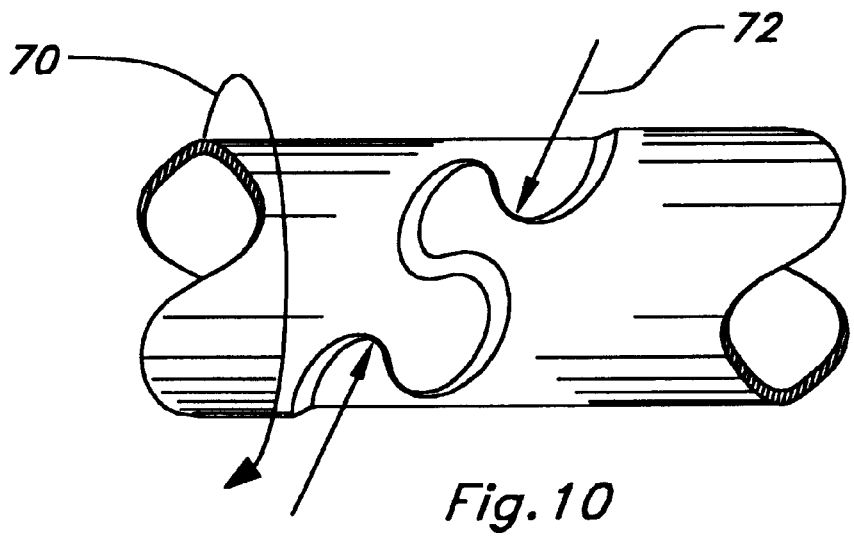
FIG. 10 is a fragmentary side view of the embodiment of FIG. 8, showing a section of the device of the present invention after being torqued in the counterclockwise direction.

The effect of the rotational forces on the flexible shaft is further shown in FIGS. 8, 9 and 10. Rotation in the direction of arrow 62 applies a force in the direction of arrow 62, at the neck region, making contact at point 60. Conversely, rotation in the direction of arrow 70 applies a force in the direction of arrow 70 at the neck region, making contact at point 72.

FIG. 11 shows the design of a flexible connector 90 which can be inserted between, for example, between a rotary power supply and an inflexible or moderately flexible shaft. The flexible connector can be used to provide power transmission between misaligned parts as previously described. In this embodiment, advantageously, a plurality of slots 92, 94 and 96 can be used, as shown in FIG. 11.

FIG. 2 shows the design of a flexible shaft or connector 100 in which an elastomer or otherwise flexible material is interposed within the slot 102 to further enhance the flexibility of the shaft and to alter the torsional response or stiffness of the member. The elastomer can be used as a shock absorbing or cushioning member. To facilitate manufacture, to provide protection of the tubular member, to provide a fluid conduit or for other reasons, the elastomer can encapsulate the entire shaft or coupler, thus forming a tubular construction 104.

In a preferred embodiment of the invention the flexible shaft is to be used as a flexible shaft for reaming the medullary canal of bones, the shaft must have a diameter less than that of the reamer which typically has a cutting diameter of about two tenths of an inch up to less than three quarters of an inch. The spiral pattern shown in U.S. Pat. No. 2,515,365 cannot be applied to this application. The three quarter inch or less shaft must have a higher spiral frequency (lower helix angle) and fewer superimposed slot cycles to provide the required combination of structural strength and flexibility. As show in FIG. 12, during the reaming of the medullary canal of the femur it is preferred that the shaft be able to flex, up to about 45 degrees. The flexible shaft indicated generally as 80 has the advantage of providing an ability to ream the medullary canal of the femur 82 with the driven end 84 of the shaft at roughly a right angle to the axis of the femur The use of a highly flexible reamer end 86 permits for ease of guiding the reamer through the bone fragments 85, 87 and 89.

What is claimed is:

1. A flexible shaft comprising an elongated tubular member of substantial wall thickness, said tubular member having:
   (i) a first end;
   (ii) a second end; and
   (iii) a center section, said center section being positioned between said first end and said second end, said center section having a slot extending in a generally helical serpentine path around and along said tubular member center section, said helical path having from about 1 to about 4 cycles per revolution, said slot having a substantial length and width of up to about 0.075 of an inch, said tubular member having a diameter in the range from about 0.15 to four inches, a helical angle of up to about 20 degrees, and a ratio of amplitude of said serpentine path to pitch in the range from greater than 0.1 to 0.5.

2. A flexible shaft comprising an elongated tubular member of substantial wall thickness, said tubular member having:
   (i) a first end;
   (ii) a second end; and
   (iii) a center section, said center section being positioned between said first end and said second end, said center section having a slot extending in a generally helical serpentine path around and along said tubular member center section, said slot having a substantial length and width said tubular member having a diameter in the range from about 0.15 to four inches and said helical path having from about 1 to about 4 cycles per revolution.

3. The flexible shaft of claim 2, further comprising, a slot width of up to about five thirty seconds of an inch, a ratio of amplitude of said serpentine path to pitch in the range from greater than 0.1 to 0.5 and a helical angle of up to about 20 degrees.

4. The flexible shaft of claim 2, wherein said slot is under cut at an angle to a radial line or a plane tangential to the surface of the shaft at the slot, said angle being at least about 15 degrees from the perpendicular.

5. A flexible shaft comprising an elongated tubular member of substantial wall thickness, said tubular member having:
   (i) a first end;
   (ii) a second end; and
   (iii) a center section, said center section being positioned between said first end and said second end, said center section having a slot extending in a generally helical serpentine path around and along said tubular member center section, said slot having a substantial length and width, said tubular member having a diameter in the range from about 0.15 to four inches and a ratio of amplitude of said serpentine path to pitch in the range from greater than 0.1 to 0.5.

6. The flexible shaft of claim 5, further comprising, a slot width of up to about 0.075 of an inch, a helical angle of up to about 20 degrees, and said helical path having from about 1 to about 4 cycles per revolution.

7. A flexible shaft comprising an elongated tubular member of substantial wall thickness, said tubular member having:
   (i) a first end;
   (ii) a second end; and
   (iii) a center section, said center section being positioned between said first end and said second end, said center section having a slot extending in a generally helical serpentine path around and along said tubular member center section, said slot having a substantial length and width, said tubular member having a diameter in the range from about 0.15 to four inches and the ratio of the diameter of the inside diameter of said shaft to the outside diameter of said shaft is in the range from about 1:1.2 to about 1:3.

8. A flexible shaft comprising an elongated tubular member of substantial wall thickness, said tubular member having:
   (i) a first end;
   (ii) a second end; and
   (iii) a center section, said center section being positioned between said first end and said second end, said center section having a slot extending in a generally helical serpentine path around and along said tubular member center section, said slot having a substantial length and width and said helical path having from about 1 to about 4 cycles per revolution.

9. A flexible shaft comprising an elongated tubular member of substantial wall thickness, said tubular member having:
   (i) a first connecting section at a first end of said tubular member;
   (ii) a second connecting section at a second end of said tubular member; and
   (iv) a center section, said center section having a plurality of slots along a serpentine path, said plurality of slots having a substantial length and width extending within a region around said tubular member, wherein at least one of said plurality of slots follows a generally helical path around and along said tubular member.

10. A flexible shaft comprising an elongated tubular member of substantial wall thickness, said tubular member having:
    (i) a first connecting section at a first end of said tubular member;
    (ii) a second connecting section at a second end of said tubular member; and
    (iii) a center section, said center section having a slot along a serpentine path, said slot having a substantial length and width extending in a generally helical path within a region around and along the tubular member and being at least partially filled with a resilient material;
    wherein said serpentine path forms a plurality of teeth and complimentary recesses on opposite sides of said slot, said slot having sufficient width to form an unbound joint, said slot width and serpentine path permitting limited movement in all directions between the teeth and the recesses, thereby providing limited flexibility in all directions upon application of tensile, compressive, or torsion forces to said shaft.

11. The flexible shaft of claim 10, wherein said resilient material is an elastomer compound of sufficient thickness to encapsulate substantially the entire shaft thus forming an enclosed member.

12. The flexible shaft of claim 11, wherein said center section slot is a plurality of slots, at least two of said plurality of slots following a serpentine path around and along said tubular member.

13. The flexible shaft of claim 10, wherein said center section slot is a plurality of slots, wherein at least two of said plurality of slots follow a serpentine path around and along the tubular member.

14. The flexible shaft of claim 10, wherein the ratio of the diameter of the inside diameter of said shaft to the outside diameter of said shaft is in the range from about 1:1.2 to about 1:3, the slot width is in the range from about 0.005 inch to 0.075 inch, in the ratio of the amplitude of said serpentine path to the pitch of said slot is in the range from greater than 0.1 to about 0.5, said helical path has a helix angle in the range of about 10 degrees to about 20 degrees, said shaft has a diameter in the range from about 0.15 inch to about 4.00 inch.

15. The flexible shaft of claim 10, wherein said slot is under cut at an angle to a radial line or a plane tangential to the surface of the shaft at the slot, said angle being at least about 15 degrees from the perpendicular.

16. The flexible shaft of claim 10, further comprising a plurality of slots, wherein at least one of said plurality of slots starts on a first plane perpendicular to said tubular member's long axis and at least another of said plurality of slots starts on a sequential plane perpendicular to said tubular member's long axis.

17. A flexible shaft comprising an elongated tubular member of substantial wall thickness, said tubular member having:

(i) a first connecting section at a first end of said tubular member;

(ii) a second connecting section at a second end of said tubular member; and (iii) a center section, said center section having a slot along a serpentine path, said slot having a substantial length and width extending in a generally helical path within a region around and along the tubular member, said center section being covered with a resilient elastomer material of sufficient thickness to encapsulate substantially the entire shaft to form an enclosed member, wherein said serpentine path forms a plurality of teeth and complimentary recesses on opposite sides of said slot, said slot having sufficient width form an unbound joint, said slot width and serpentine path permitting limited movement in all direction between the teeth and the recesses, thereby providing limited flexibility in all directions upon application of tensile, compressive, or torsion forces to said shaft.

18. The flexible shaft of claim 17, wherein said center section slot is a plurality of slots, wherein at least two of said plurality of slots follow a serpentine path around and along the tubular member.

19. The flexible shaft of claim 17, wherein the ratio of the diameter of the inside diameter of said shaft to the outside diameter of said shaft is in the range from about 1:1.2 to about 1:3, the slot width is in the range from about 0.005 inch to 0.075 inch, in the ratio of the amplitude of said serpentine path to the pitch of said slot is in the range from greater than 0.1 to about 0.5, said helical path has a helix angle in the range of about 10 degrees to about 20 degrees, said shaft has a diameter in the range from about 0.15 inch to about 4.00 inch.

20. The flexible shaft of claim 17, wherein said slot is under cut at an angle to a radial line or a plane tangential to the surface of the shaft at the slot, said angle being at least about 15 degrees from the perpendicular.

21. The flexible shaft of claim 17, wherein at least one of said plurality of slots starts on a first plane perpendicular to said tubular member's long axis and at least another of said plurality of slots starts on a sequential plane perpendicular to said tubular member's long axis.

* * * * *